(12) United States Patent
Schatzmayr et al.

(10) Patent No.: US 11,690,881 B2
(45) Date of Patent: Jul. 4, 2023

(54) **USE OF *CORIOBACTERIIA* TO PROMOTE GUT HEALTH**

(71) Applicant: ERBER AKTIENGESELLSCHAFT, Getzersdorf (AT)

(72) Inventors: Dian Schatzmayr, Tulln (AT); Eva Maria Binder, Tulln (AT); Veronika Nagl, Böheimkirchen (AT); Gerd Schatzmayr, Tulln (AT)

(73) Assignee: ERBER AKTIENGESELLSCHAFT, Getzersdorf (AT)

( * ) Notice: Subject to any disclaimer, the term of this patent is extended or adjusted under 35 U.S.C. 154(b) by 0 days.

(21) Appl. No.: 16/955,706

(22) PCT Filed: Dec. 19, 2018

(86) PCT No.: PCT/EP2018/085807
§ 371 (c)(1),
(2) Date: Jun. 18, 2020

(87) PCT Pub. No.: WO2019/121891
PCT Pub. Date: Jun. 27, 2019

(65) Prior Publication Data
US 2020/0338138 A1 Oct. 29, 2020

(30) Foreign Application Priority Data
Dec. 22, 2017 (EP) .................................... 17210273

(51) Int. Cl.
| | |
|---|---|
| A61K 35/741 | (2015.01) |
| A23K 50/30 | (2016.01) |
| A23K 50/60 | (2016.01) |
| A23K 10/18 | (2016.01) |
| C12P 7/42 | (2006.01) |
| A61K 35/00 | (2006.01) |

(52) U.S. Cl.
CPC ............ *A61K 35/741* (2013.01); *A23K 10/18* (2016.05); *A23K 50/30* (2016.05); *A23K 50/60* (2016.05); *C12P 7/42* (2013.01); *A61K 2035/115* (2013.01)

(58) Field of Classification Search
None
See application file for complete search history.

(56) References Cited

U.S. PATENT DOCUMENTS

| 6,794,175 B1 | 9/2004 | Eva-Maria et al. |
| 7,347,997 B1 | 3/2008 | Binder et al. |
| 2011/0142991 A1 | 6/2011 | Eva-Maria et al. |

FOREIGN PATENT DOCUMENTS

| WO | 2006033951 A1 | 3/2006 |
| WO | 2010125421 A1 | 11/2010 |
| WO | 2016183535 A1 | 11/2016 |
| WO | 2018002671 A1 | 1/2018 |

OTHER PUBLICATIONS

EFSA FEEDAP Panel (EFSA Panel on Additives and Products or Substances used in Animal Feed) (2013) "Scientific Opinion on the safety and efficacy of micro-organism DSM 11798 when used as a technological feed additive for pigs", EFSA Journal, 11(5):3203, 36 pages.
Levanova, et al. (2017) "Systematics, taxonomy and classification of bacteria", Fundamental And Clinical Medicine, 2(1):91-101.
Patel, et al. (2010) "Probiotic bile salt hydrolase: Current developments and perspectives", Applied Biochemistry and Biotechnology, 162:166-180.
Rychen, et al. (2017) "Safety and efficacy of microorganism DSM 11798 as a technological additive for all avian species", Scientific Opinion, EFSA Journal, 15(1):4676, 24 pages.
Münch, A., et al. (2007) "Dihydroxy bile acids increase mucosal permeability and bacterial uptake in human colon biopsies", Scandinavian Journal of Gastroenterology, 42:1167-1174.
Altschul (1993) "A Protein Alignment Scoring System Sensitive at All Evolutionary Distances", J Mol Evol, 36:290-300.
Altschul et al (1997) "Gapped BLAST and PSI-BLAST: a new generation of protein database search programs", Nucleic Acids Research, vol. 25, 17: 3389-3402.
Brutlag, et al (1990) "Improved sensitivity of biological sequence database searches", CABIOS vol. 6, 3:237-245.
Connor, et al (2016) "Glucagon-like peptide 2 and its beneficial effects on gut function and health in production animals", Domestic Animal Endocrinology 56:S56-S65.
Diego-Cabero et al, (2015) "Bile acid mediated effects on gut integrity and performance of early-weaned piglets", BMC Veterinary Research, 11:111.
Derikx, et al, (2010) "Non-invasive markers of gut wall integrity in health and disease", World J Gastroenterol, 16(42): 5272-5279.
Grootjans, et al, (2010) "Non-invasive assessment of barrier integrity and function of the human gut", World J Gastrointest Surg, 2(3): 61-69.
Henikoff et al (1992) "Amino acid substitution matrices from protein blocks", Proc. Natl. Acad. Sci. USA 89:10915-10919.
Kawamata, et al (2003) "A G Protein-coupled Receptor Responsive to Bile Acids*", The Journal of Biological Chemistry, vol. 278, 11:9435-9440.
Slavin (2013) "Fiber and Prebiotics: Mechanisms and Health Benefits", Nutrients 5:1417-1435.
Wijtten, et al (2011) "Intestinal barrier function and absorption in pigs after weaning: a review", British Journal of Nutrition, 105:967-981.

*Primary Examiner* — Jennifer E Graser
(74) *Attorney, Agent, or Firm* — Kagan Binder, PLLC (57) ABSTRACT

The present invention relates to a use of a microorganism of the class Coriobacteriia for promoting gut health of a healthy subject. Also provided is a method for the production of chenodeoxycholic acid (CDCA) and a method for the production of lithocholic acid (LCA).

14 Claims, 3 Drawing Sheets
Specification includes a Sequence Listing.

FIGURE 1:

| Sample Identification | Specification | GCDCA (μM) | CDCA (μM) |
|---|---|---|---|
| C1_t0 | GCDCA | 4.15 | 0 |
| C1_t48 | | 4.16 | 0 |
| C2_t0 | GCDCA + inactivated BBSH 797 | 4.38 | 0 |
| C2_t48 | | 4.60 | 0 |
| T_t0 | GCDCA + BBSH 797 | 1.59 | 0,02 |
| T_t48 | | 1.41 | 1,06 |

FIGURE 2:

| Bile acid | group A [nM] | Group B [nM] | p |
|---|---|---|---|
| Glycolithocholic Acid | 26,6 ± 10,6a | 49,3 ± 18,7b | 0.010 |
| Taurolithocholic Acid | 9.2 ± 2.6a | 13.8 ± 5.1b | 0.040 |

FIGURE 3:

USE OF *CORIOBACTERIIA* TO PROMOTE GUT HEALTH

CROSS-REFERENCE TO RELATED APPLICATIONS

This application claims priority to International Application No. PCT/EP2018/085807, filed on Dec. 19, 2018, which claims the benefit of EP Application No. 17210273.3, filed on Dec. 22, 2017, wherein the contents of said applications are incorporated herein by reference in their entireties. Also, the entire contents of the ASCII text file entitled "IPM0099US_Sequence_Listing.txt" created on Jun. 17, 2020, having a size of 5 kilobytes is incorporated herein by reference.

TECHNICAL FIELD OF THE INVENTION

The present invention relates to a use of a microorganism of the class Coriobacteriia for promoting gut health of a healthy subject. Also provided is a method for the production of chenodeoxycholic acid (CDCA) and a method for the production of lithocholic acid (LCA).

DESCRIPTION

In the common biomedical literature bile acids or bile salts have 24 carbon atoms and are abbreviated as $C_{24}$ bile acids, in contraposition to "primitive" bile acids, which have 25-27 carbon atoms ($C_{27}$, $C_{26}$, $C_{25}$ bile acids) and are present in the bile acid pool of primitive (e.g. coelacanth and sharks) and less primitive (e.g. reptiles and amphibians) vertebrates. In higher vertebrates, $C_{24}$ bile acids constitute a major part of the bile (Hofmann et al. (1992) "A proposed nomenclature for bile acids" Lipid Res. 1992 April; 33(4):599-604). The liver synthesizes bile acids at the expense of cholesterol and also retrieves reabsorbed bile acids from the blood. From hepatocytes they are secreted against steep concentration gradients into bile, together with cholesterol and phospholipids. Thus, between meals, most of the pool of bile acids resides in the gallbladder ready to be used at short notice.

Primary bile acids are those synthesized as such by the liver, and comprise predominantly cholic acid (CA), and chenodeoxycholic acid (CDCA). These are secreted to bile mainly conjugated with glycine and taurine, thus having enhanced water solubility. Upon release in the intestine bile acids promote absorption of dietary fats and fat-soluble vitamins.

Secondary bile acids are derived from primary bile acids by modifications carried out by intestinal bacteria. The main modifications are deconjugation, oxidation of hydroxyl groups in 3, 7 and 12 positions, and 7-dehydroxylation. The main secondary bile acids are lithocholic acid (LCA) and deoxycholic acid (DCA).

However, bile acids not only play a role in digestion but also have effects on health and disease. In addition, they function as signaling molecules. For example, bile acids can influence, as one of multiple factors, the composition of gut microbiota or exert anti-microbial activities (Boesjes and Brufau (2014) "Metabolic effects of bile acids in the gut in health and disease" Current Medicinal Chemistry, 21, 2822-2829).

In particular, bile acids mediate effects on gut integrity and performance of early-weaned piglets. Available evidence indicates that activating intestinal signaling pathways controlled by bile acids allows stimulating the release of endogenous GLP-2 thereby improving gut integrity in experimental models of intestinal atrophy and dysfunction (de Diego-Cabero et al. (2015) "Bile acid mediated effects on gut integrity and performance of early-weaned piglets." BMC veterinary research 11:111).

In this context it is noted that intestinal barrier and gut health in general determine the amount of pathogens that can migrate from the intestinal lumen into the body, which subsequently increases the susceptibility to disease. In addition, the better the intestinal epithelium functions the more nutrients are absorbed, which in turn determines the growth capacity of animals. The health of the intestinal barrier thus has a significant impact on the welfare of the animals.

In principle, three different strategies can be distinguished in order to strengthen the intestinal barrier e.g. of piglets in the weaning phase:
1) Improvement of the palatability of the feed to increase feed intake;
2) Addition of essential nutrients to compensate for the losses caused by a damaged intestinal barrier;
3) Addition of biologically active substances that strengthen the intestinal barrier.

In order to counteract the above described problems and defects, it was necessary to develop a feeding concept that is effective in weaner piglets on the one hand, and can be applied easily under practical conditions on the other hand.

Furthermore, there was a need in the art to develop methods/uses to promote gut health in healthy subjects.

The solution of the present invention is described in the following, exemplified in the examples, illustrated in the Figures and reflected in the claims.

The present invention relates to a use of a microorganism of the class Coriobacteriia for promoting gut health of a healthy subject.

In addition, the present invention relates to a method for the production of chenodeoxycholic acid (CDCA), the method comprising
a) contacting a microorganism of the class Coriobacteriia with a glycochenodeoxycholic acid (G-CDCA);
thereby obtaining chenodeoxycholic acid.

Also provided is a method for the production of lithocholic acid (LCA), the method comprising
a) contacting a microorganism of the class Coriobacteriia with a chenodeoxycholic acid (CDCA) thereby obtaining litocholic acid.

The present invention also relates to a method for promoting gut health of a healthy subject, the method comprising
a) contacting a microorganism of the class Coriobacteriia with the subject.

It was surprisingly found that a microorganism of the class Coriobacteriia, namely of the strain DSM 11798, promotes gut health of a subject. The present inventors discovered a feeding strategy that strengthens the intestinal barrier of subjects. This is achieved by the addition of the bacterium BBSH 797 (genus novus of the family Eggerthellaceae), strain number 11798 (DSM 11798) into subject's feed.

Addition of BBSH 797 to feed lead to significant increase in the bile acids glycolithocholic acid and taurolithocholic acid in weaners. These bile acids act as messengers and initiate molecular cascades that ultimately lead to a significant improvement in gut integrity in weaned piglets. More precisely, supplementation with BBSH 797 results in a specific elevation of glycolithocholic acid and taurolithocholic acid in weaned piglet plasma. This is of biological relevance as these substances act as strong natural agonists at TGR5 receptors (Schaap et al. (2014) "Bile acid receptors as targets for drug development" Nature Reviews Gastroenterology & Hepatology 11(1):55-67; Kawamata et al. (2003) "A G protein-coupled receptor responsive to bile acids*" vol. 278, no. 11, pp. 9435-9440). These receptors are located in the cell membrane of certain intestinal epithelial cells (L cells). Upon activation these receptors trigger a cascade, which ultimately leads to the release of the peptide glucagon-like peptide 2 (GLP-2).

Notably, exogenous GLP-2 can restore mucosal growth, transcellular transport, and the expression of tight junction proteins that control paracellular permeability. Further, chronic administration of GPL-2 can increase villus height and crypt depth in the small intestine and colon. It has also been shown that administration of a long-acting analog of GPL-2 can increase intestinal weight and enzyme activity. Some of these positive effects of GPL-2 were obtained in early weaned animals (de Diego-Cabero et al. (2015) "Bile acid mediated effects on gut integrity and performance of early-weaned piglets." BMC veterinary research 11:111). Similarly, Connor et al. (2016) found that GPL-2 initiates a variety of intestinal reactions leading to increased gut health, most notably strengthening the gut barrier (Connor et al. (2016) "Glucagon-like peptide 2 and its benefcial effects on gut function and health in production animals" Domestic Animal Endocrinology 56, S56-S65).

Further experiments conducted by the present inventors showed that there is a correlation between elevated bile acid concentrations of glycolithocholic acid and taurolithocholic acid and/or the administration of BBSH 797 with an improved intestinal barrier. The integrity of the intestinal barrier was assessed using a dual-sugar assay. The principle of this test is based on co-administration of lactulose and rhamnose. The disaccharide lactulose enters the bloodstream only paracellularly through the narrow gaps between the individual intestinal epithelial cells. On the other hand, monosaccharide rhamnose are transported into the body both paracellularly and transcellularly through the intestinal cells. When the intestinal barrier weakens, the interstitial space becomes increasingly porous, as a result of which comparatively larger amounts of disaccharides are absorbed. Consequently, the lactulose/rhamnose ratio in the urine increases. An intact or strengthened intestinal barrier is associated with a reduced lactulose/rhamnose ratio in the urine (Wijtten et al., (2011) "Intestinal barrier function and absorption in pigs after weaning: a review." Br J Nutr 105:967-981). The Examples of the present application show that administration of BBSH 797 for several weeks resulted in a significantly reduced urinary lactulose/rhamnose ratio. This proofs that the integrity of the intestine is strengthened upon BBSH 797 application. Consequently, the gut health is promoted by BBSH 797.

In addition, it was surprisingly found in in vitro experiments that BBSH 797 is capable of converting glycochenodeoxycholic acid to chenodeoxycholic acid. According to the literature, the latter can lead to a release of GLP-2. As explained in de Diego-Cabero an increase in GLP-2 results in an improved intestinal integrity (de Diego-Cabero et al. (2015) "Bile acid mediated effects on gut integrity and performance of early-weaned piglets." BMC veterinary research 11:111).

Thus, the present invention relates to a use of a microorganism of the class Coriobacteriia for promoting gut health of a healthy subject.

As used herein a "microorganism of the class Coriobacteriia" can be any microorganism of the class Coriobacteriia. The taxonomic classification of the class Coriobacteriia as described herein is based on Gupta et al. (2013) "Molecular signatures for the class Coriobacteriia and its different clades; proposal for division of the class Coriobacteriia into the emended order Coriobacteriales, containing the emended family Coriobacteriaceae and Atopobiaceae fam. nov., and Eggerthellales ord. nov., containing the family Eggerthellaceae fam. nov." Int. J. Syst. Evol. Microbiol. 63 (Pt 9), pp. 3379-3397 as well as on the NCBI Taxonomy Browser (https://www.ncbi.nlm.nih.gov/Taxonomy/Browser/www-tax.cgi, version that was online available Oct. 15, 2017) as well as on the LPSN bacterioi.net online tool (http://www-.bacterio.net/eggerthella.html, version that was online available Oct. 15, 2017).

Exemplary orders of microorganisms that are embraced by the class Coriobacteriia are the order Coriobacteriales and the order Eggerthellales. It is envisioned that the microorganism used in the present invention is a microorganism of the order Coriobacteriales or the order Eggerthellales. It is further envisioned that the microorganism used in the present invention is a microorganism of the order Coriobacteriales. It is also contemplated that the microorganism used in the present invention is a microorganism of the order Eggerthellales.

A microorganism of the order Coriobacteriales can comprise any microorganism within the order Coriobacteriales. Exemplary families included in the order Coriobacteriales are for example Atopobiaceae, Coriobacteriaceae and unclassified Coriobacteriales. A microorganism of the order Eggerthellales can comprise any microorganism within the order Eggerthellales. Exemplary families included in the order Eggerthellales are for example Eggerthellaceae and unclassified Eggerthellales. It is envisioned that the microorganism used in the present invention is a microorganism of the family Coriobacteriaceae. It is also contemplated that the microorganism used in the present invention is a microorganism of the family Eggerthellaceae.

Exemplary genera included in the family Atopobiaceae are for example *Atopobium, Libaniococcus, Olsenella* and unclassified Atopobiaceae. Exemplary genera included in the family Eggerthellaceae are for example *Adlercreutzia, Arabia, Asaccharobacter, Cryptobacterium, Denitrobacterium, Eggerthella, Enterorhabdus, Gordonibacter, Paraeggerthella. Phonicibacter, Raoultibacter, Slackia* and unclassified Eggerthellaceae. The present invention contemplates that the microorganism used in the present invention is of the genus unclassified Eggerthellaceae. Exemplary genera included in the family Coriobacteriaceae are for example *Collinsella, Coriobacterium* and unclassified Chriobacteriales. It is envisioned that the microorganism used in the present invention is a microorganism of the family Eggerthellaceae. It is envisioned that the microorganism used in the present invention is a microorganism of the genus DSM11798.

It is further envisioned that the microorganism used in the present invention can be a microorganism of the strain DSM11798 also referred to as BBSH 797 herein. DSM11798 was deposited with DSMZ-DEUTSCHE SAMMLUNG VON MIKROOGANISMEN UND ZELLKULTUREN GmbH, Mascheroder Weg 1 b, D-38124 Braunschweig, Germany, on Sep. 17, 1997.

It is contemplated that the microorganism used in the present invention can comprise a nucleic acid molecule that has a sequence identity of at least 70%, 80%, 85%, 90%, 95%, 98%, 99% or 100% to a sequence of SEQ ID NO. 1 (16S-RNA sequence of DSM11798) and or SEQ ID NO: 2.

As used herein the term "nucleic acid molecule" or "nucleic acid" encompasses any nucleic acid molecule having a nucleotide sequence of bases comprising purine- and pyrimidine bases, which are comprised by said nucleic acid molecule, whereby said bases represent the primary structure of a nucleic acid molecule. Nucleic acid sequences can include DNA, cDNA, genomic DNA, RNA, both sense and antisense strands, or may contain non-natural or derivatized nucleotide bases, as will be readily appreciated by those skilled in the art. A polynucleotide can be composed of any polyribonucleotide or polydeoxribonucleotide, which may be unmodified RNA or DNA or modified RNA or DNA. The term "RNA" may include any RNA molecule. Exemplary RNA molecules include messenger RNA (mRNA), transfer RNA or ribosomal RNA. The nucleic acid molecule may be a 16S rRNAs.

A variety of modifications can be made to DNA and RNA; thus, the term "nucleic acid molecules" can embrace chemically, enzymatically, or metabolically modified forms. "Modified" bases include, for example, tritylated bases and unusual bases such as inosine. Modified nucleic acid molecules can for example be used in methods for detection of nucleic acid molecules described herein.

In accordance with the present invention, the term "identical" or "percent identity" in the context of two or more nucleic acid molecules refers to two or more sequences or subsequences that are the same, or that have a specified percentage of nucleotides that are the same (e.g., at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 80% to 95% or greater sequence identity are considered to be substantially identical. Such a definition also applies to the complement of a test sequence. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Also available to those having skill in this art are the BLAST and BLAST 2.4 algorithms (Altschul Nucl. Acids Res. 25 (1977), 3389-3402). The BLASTN program for nucleic acid sequences uses as defaults a word size (W) of 28, an expect threshold of 10, and a comparison of both strands. Furthermore, the BLOSUM62 scoring matrix (Henikoff Proc. Natl. Acad. Sci., USA, 89, (1989), 10915) can be used.

For example, BLAST2.4, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments.

Methods to obtain a microorganism used in the present invention are known to the skilled artesian. Usually this takes isolation of the microorganism used in the present invention from a source e.g. DSM11799. Then the microorganism can be grown in a culture or in a fermentation solution. Alternatively a source comprising the microorganism can be directly grown in culture or in a fermentation solution. After growing the microorganism may be purified. It is also envisioned that the culture or fermentation solution in which the microorganism has been grown is used.

For example such a microorganism can be obtained as described in WO 99/35240. As described therein the strain DSM 11798 can be obtained from the co-culture of DSM 11799. Notably, the strain DSM 11798 and DSM 11799 have also been deposited with DSMZ-DEUTSCHE SAMMLUNG VON MIKROOGANISMEN UND ZELLKULTUREN GmbH, Mascheroder Weg 1 b, D-38124 Braunschweig, Germany, on Sep. 17, 1997. DSM 11798 is also commercially available in Mycofix® Plus 5.Z formula (DSM Austria GmbH).

The active gram positive bacteria BBSH 797 (DSM 11798) was originally (and repeatedly) isolated from several bovine rumen contents under standard anaerobic condition using antibiotics targeting gram negative bacterial. Methods to isolate and obtain a microorganism of interest are known to the skilled person.

It is further contemplated that the microorganism used in the present invention can be an anaerobic gram-positive bacterium. Additionally or alternatively the microorganism used in the present invention can have a rod-like appearance. Additionally or alternatively the microorganism used in the present invention can be non-spore-forming. Additionally or alternatively the microorganism used in the present invention can be 0.1 to 3 μm long. It may occur both individually, in pairs or in long chains, in particular up to approximately 150 μm. The person skilled in the art knows how to measure such parameters.

Additionally or alternatively the microorganism used in the present invention can be capable of converting G-CDCA into CDCA as also described elsewhere herein. Additionally or alternatively the microorganism used in the present invention can be capable of converting CDCA into LCA as also described elsewhere herein.

The microorganism used in the present invention can be used as a 'whole' single cell microorganisms and thus visibly intact microorganisms. It is also contemplated that the microorganism used in the present invention can be a viable or living microorganism.

Also envisioned is that a preparation of the microorganism can be used. This means that the microorganisms may not be present as a whole but may be present as cellular fragments or that its DNA and/or 16SrRNA, or specific enzymes of the microorganism are present.

For example, to detect that BBSH 797 is present in a composition or if BBSH 797 has been used in the present invention analysis of the 16SrRNA sequence using standard methods of DNA extraction, PCR amplification of the DNA coding for the 16SrRNA and DNA sequencing of the PCR amplicon can be performed.

Additionally or alternatively especially for a composition such as feed real-time polymerase chain reaction (qPCR) can be used for detection and identification of BBSH 797. Therefore, DNA can be extracted and purified from samples/compositions with standard methods. The qPCR detection can be based on the detection of marker genes, like the BBSH 797 16SrRNA gene sequence as shown in SEQ ID NO. 1 (additionally or alternatively also the cpn60 gene as shown in SEQ ID NO. 2). Since the 16SrRNA gene contains conserved and variable regions, for specific detection of BBSH 797 primers can be targeting variable regions as described in Matsuki et al. 2004, allowing specific amplification of BBSH 797 RNA sequence from samples like feed material (Matsuki et al. (2004) "Use of 16S rRNA Gene-Targeted Group-Specific Primers for Real-Time PCR Analysis of Predominant Bacteria in Human Feces." Applied and Environmental Microbiology 70(12): 7220-7228). Within the qPCR reaction, the obtained fluorescence signal is proportional to the amount of the PCR product and give information about presence of the target sequence in the sample. Melting curve analysis gives further information about the specificity of the amplicon, showing sequence dependent melt behavior.

Thus, the term microorganism also embraces preparations of the microorganism. The present invention also contemplates that the microorganism is used as a preparation of the microorganism. Such a preparation can also comprise further molecules and/or proteins and/or substances e.g. a left over from a buffer used when isolating and/or growing the microorganism used in the present invention.

The microorganism used in the present invention may be provided within a composition. In principle, the microorganism may be provided within any composition suitable for the uses and methods of the present invention.

Thus, the present invention also relates to a use of a composition, comprising a microorganism of the class Coriobacteriia for promoting gut health of a healthy subject. Exemplary compositions include food compositions, feed compositions, liquid compositions e.g. for drinking purposes. It is envisioned that the microorganism used in the present invention can be provided within a food- and/or feed composition. The microorganism used in the present invention can also be provided as a feedstuff additive or a preparation of a feedstuff additive.

Therefore, the present invention also relates to the use of a microorganism of the class Coriobacteriia for preparation of a composition for promoting gut health of a healthy subject.

Methods to prepare such food- and/or feed compositions are known to the skilled person and are inter alia described in WO 99/35240.

For example, a culture or fermentation solution comprising the microorganism used in the present invention can be concentrated e.g. by centrifuging or filtering and/or stabilization, in particular by freeze- or spray-drying or encapsulating. In this connection, for example, culture or fermentation solution comprising the microorganism used in the present invention can be concentrated in a first step by removing liquid by centrifuging or filtering, and/or carrying out the stabilization directly from the fermentation solution. It is also envisioned that a filler, release agent and/or carrier material, such as aluminium silicates, diatomaceous earth, carbohydrates, sugar alcohols, starches, milk and whey powder, protein hydrolysates, yeasts, seaweed meal and/or polyvinylpolypyrrolidone (PVPP) are present in the composition as described herein. It is also envisioned that yeast and/or seaweed meal are added as carriers. It is also envisioned that diatomaceous earth is added as release agent. By addition of these carriers or fillers, it is e.g. possible in the following stabilization step such as the freeze-drying, spray-drying, encapsulation of pelletization step, to obtain a solid product in which a culture of the microorganism used in the present invention can be deposited directly on a carrier. The microorganism or its mixed culture may be deposited on a substance having a large internal surface area, such as argillaceous earths, aluminum silicates, zeolites and the like. In particular, the microorganism may be deposited onto yeast and/or seaweed meal.

The composition may additionally or alternatively comprise a carrier material and/or filler and/or release agent. By means of the addition of carrier materials and/or fillers, it is possible, if desired, to bind harmful substances to be degraded, which can be contained in the feedstuff, physically to the substances, as a result of which they are no longer available for metabolization. In this case, in particular, aluminium silicates, diatomaceous earth, carbohydrates, sugar alcohols, starch, milk and whey powder, protein hydrolysates, yeasts and/or polyvinylpolypyrrolidone can be employed as a carrier material and/or filler.

The composition used in the present invention may comprise the spray- or freeze-dried microorganism of the class Coriobacteriia of 1 to 99% by weight, preferably from 0.5 to 1% by weight, and/or 99 to 1% by weight, of carrier material and/or filler.

The composition may be a feedstuff additive. The feedstuff additive may be applied in an amount of 0.1 to 8.0 kg/1000 kg composition such as feed/food composition, in particular 0.5 to 2.0 kg/1000 kg composition such as feed/food composition.

The composition may additionally or alternatively comprise one or more probiotics. "Probiotics" as used herein are microorganisms that are believed to provide health benefits when consumed. Probiotics have to be alive when administered. In principle any probiotic can be used. The person skilled in the art knows probiotics suitable for use in the present invention.

The composition may thus comprise one or more microorganism(s) different from the microorganism used in the present invention. In principle, any suitable microorganism may be added to the composition. Exemplary microorganisms include *Bacteroides fragilis, B. vulgatus, Listeria monocytogenes* and species of *Lactobacillus* and *Bifidobacterium* such as *Bifidobacterium bifidum* or its biologically functional equivalent, *Clostridium* such as *Clostridium perfringens* and Eubacteria.

The composition may additionally or alternatively comprise one or more prebiotics. "Prebiotics" as used herein are food ingredients that induce the growth or activity of beneficial microorganisms (e.g., bacteria and fungi). More precisely a prebiotic may be a selectively fermented ingredient that allows specific changes, both in the composition and/or activity in the gastrointestinal microflora, that confer benefits. In principle any prebiotic can be used. The person skilled in the art knows prebiotics suitable for use in the present invention.

Prebiotics can be non-digestible fiber compounds that pass undigested through the upper part of the gastrointestinal tract and stimulate the growth or activity of advantageous bacteria that colonize the large bowel by acting as substrate for them. Foods that comprise prebiotics and that can be added to the composition include Gum Arabic, Raw, Dry Chicory Root Raw, Dry Jerusalem Artichoke Raw, Dry Dandelion Greens Raw, Dry Garlic Raw, Dry Leek Raw, Dry Onion Raw Asparagus Raw Wheat bran Whole Wheat flour, and Cooked Raw Banana. The prebiotic may also comprise a fiber as described in Slavin (2013) "Fiber and Prebiotics: Mechanisms and Health Benefits" Nutrients. 5(4): 1417-1435. The prebiotic may also be a galactooligosaccharid.

Therefore, the composition may additionally or alternatively comprise one or more sources of galactooligosaccharides. For example the composition may further comprise one or more of liquid milk, dried milk powder such as whole milk powder, skimmed milk powder, fat filled milk powders, whey powders, fermented dairy products, beverages, cereals, bread, food and feed supplements, dietary supplements, animal feeds, poultry feeds or indeed any other food or beverage. Further galactooligosaccharides and how galactooligosaccharides can be obtained is for example described in Torres et al. (2010) "Galacto-Oligosaccharides: Production, Properties, Applications, and Significance as Prebiotics" Comprehensive Reviews in Food Science and Food Safety, Volume 9, Issue 5, p. 438-454.

The composition may additionally or alternatively comprise at least one component selected from the group of vitamins, minerals, enzymes and components for detoxifying mycotoxins. The enzyme may be selected from the group of proteases, amylases, cellulases or glucanases, hydrolases, lipolytic enzymes, mannosidases, oxidases, oxidoreductases, phytases and xylanases and/or combinations thereof. Mycotoxin detoxifying components may be selected from the mycotoxin detoxifying enzymes such as aflatoxin oxidase, ergotamine hydrolases, ergotamine amidases, ochratoxin amidases, fumonisin carboxylesterases, fumonisin aminotransferases, aminopolyol aminoxidases, deoxynivalenol epoxide hydrolases, zearalenone hydrolases; or mycotoxin-detoxifying microorganisms; or mycotoxin-binding components such as microbial cell walls or inorganic materials such as bentonite. It is also envisioned that the composition may comprise bentonite and/or a fumonisin aminotransferase e.g. EC 3.1.1.87.

It is further envisioned that the microorganism or the composition used in the present invention can be provided for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70 or more days. For example, the microorganism used in the present invention can be provided for 42 or 44 days. The microorganism used in the present invention can also be provided for less than 70, 60, 50, 45, 40 or less days.

It is further contemplated that the microorganism used in the present invention can be provided in a dosage of $0.25*10^9$, $0.5*10^9$, $0.75*10^9$, $1.0*10^9$, $1.25*10^9$, $1.5*10^9$, $1.75*10^9$, $2.0*10^9$, $2.25*10^9$, $2.5*10^9$, $2.75*10^9$, $3.0*10^9$, $3.25*10^9$, $3.5*10^9$, $3.75*10^9$, $4.0*10^9$, $4.25*10^9$, $4.5*10^9$, $4.75*10^9$, $5.0*10^9$ or more colony forming units per kg The microorganism can be provided in such a dosage within a composition e.g. as food- and/or feed (composition), which can be taken up by the subject. For example, the microorganism used in the present invention can be provided in a dosage of at least $2.0*10^8$, $5.0*10^8$, $7.0*10^8$, $1.0*10^9$, $2.0*10^9$ or at least $2.2*10^9$ colony forming units per kg. The microorganism can be provided in such a dosage in a composition e.g. food- and/or feed (composition), which can be taken up by the subject. The microorganism used in the present invention can be provided in a dosage of less than $5.0*10^9$, $4.5*10^9$, $4.0*10^9$, $3.5*10^9$, $3.0*10^9$, $2.5*10^9$, $2.0*10^9$, $1.5*10^9$ or less colony forming units per kg. The microorganism can be provided in such a dosage within a composition e.g. a food- and/or feed (composition), which can be taken up by the subject. The microorganism used in the present invention can be provided in a dosage of less than $5.0*10^9$, $4.5*10^9$, $4.0*10^9$, $3.5*10^9$, $3.0*10^9$, $2.5*10^9$, $2.0*10^9$, $1.5*10^9$, $1.0*10^9$, $9.0*10^8$, $8.0*10^8$, $7.0*10^8$, $6.0*10^8$, $5.0*10^8$, $4.0*10^8$, $3.0*10^8$, $2.0*10^8$, $1.0*10^8$ or less colony forming units per kg. The microorganism can be provided in such a dosage in a composition e.g. a food- and/or feed (composition), which can be taken up by the subject. The microorganism used in the present invention can be provided in a dosage of $7.0*10^9$-$1.0*10^8$, $6.0*10^9$-$2.0*10^8$, $5.0*10^9$-$3.0*10^8$, $4.0*10^9$-$5.0*10^8$, $3.0*10^9$-$6.0*10^8$, or $2.5*10^9$-$8.5*10^8$ colony forming units per kg. The microorganism can be provided in such a dosage within a composition e.g. a food- and/or feed (composition), which can be taken up by the subject.

It is clear that when the microorganism used in the present invention is provided as a feed additive, the number of colony forming units can be much higher within that feedstuff than the number of colony forming units that is used in a final composition such as a (final or feed) feed/food composition as described herein.

As used herein the term "colony forming units" or "CFU" is a measure to estimate the number of viable bacteria in a sample. Viable is defined as the ability to multiply via binary fission under the controlled conditions. Methods to determine CFU are known to the skilled person.

Also the present invention contemplates that the microorganism used in the present invention is capable of converting or converts glycochenodeoxycholic acid (G-CDCA) into chenodeoxycholic acid (CDCA).

Further, the present invention envisions that the microorganism used in the present invention can increase the bile acid(s) glycolithocholic acid (GLCA) and/or taurolitocholic acid (TLCA) within the subject e.g. compared to the level/concentration of GLCA and/or TLCA before administration of the microorganism or compared to a proper control. For example, the bile acid(s) glycolithocholic acid (GLCA) and/or taurolitocholic acid (TLCA) can be measured in a sample such as a blood sample such as a plasma sample that has been obtained from a subject. Methods to measure the presence of GLCA and TLCA are known to the skilled person. For example, these bile acids may be measured using HPLC or a commercially available ELISA kit.

The microorganism described herein is used for promoting gut health of a healthy subject.

The term 'gut health' as described herein means the health status of the gut. Any marker/feature/morphologic aspects or the like can be used to determine gut health. Such markers/features/morphologic aspects are known to the skilled person. Exemplary methods are inter alia described in Derikx et al. (2010) "Non-invasive markers of gut wall integrity in health and disease" World Journal of Gastrology 16(42): 5272-5279.

It is further contemplated that gut health is considered promoted when the intestine integrity is increased/promoted. Thus, the present invention also relates to a use of a microorganism of the class Coriobacteriia for promoting intestinal integrity of a healthy subject.

As used herein 'intestinal integrity' means the integrity of the intestinal (epithelial) barrier. The intestinal (epithelial) barrier maintains physiological gut functions and can serve as the first line of host defense against potentially harmful stressors from the environment, such as bacteria and viruses, as well as natural antigens and toxins occurring in food. The physical intestinal barrier is primarily formed by epithelial cells, connected by tight junctions, which form a network sealing adjacent epithelial cells near the luminal surface, thus preventing a paracellular transport of luminal antigens. A breakdown of the normally impeccable epithelial barrier of the intestine results in the development of a "leaky" gut or a compromised intestinal integrity. Disintegrated intestinal tight junctions can allow the paracellular infiltration of luminal antigens and are considered as a pivotal pathogenic factor in the onset and promotion of chronic intestinal inflammations, such as inflammatory bowel disease (IBD). How, intestinal integrity (intestinal barrier function) can be assessed is known to the skilled person and for example described in Wang et al. (2015) "Methods to determine intestinal permeability and bacterial translocation during liver disease." J Immunol Methods; 421: 44-53 or Grootjans et al. (2010) "Non-invasive assessment of barrier integrity and function of the human gut" World J Gastrointest Surg; 2(3): 61-69.

For example, intestinal integrity can be considered promoted when the ratio between lactulose/rhamnose in the urine 6 hours after the subject was fed with lactulose and rhamnose is lower than the ratio between lactulose/rhamnose in the urine at the time point of feeding lactulose and rhamnose. As explained elsewhere herein, the subject can be a healthy subject.

Gut health/intestinal integrity can also be considered promoted when the bile acid glycolithocholic acid and/or taurolitocholic acid are increased to a certain extend compared to a control. For example such an increase can be an increase similar to an increase seen when the bile acid glycolithocholic acid and/or taurolitocholic acid of subjects receiving a microorganism used in the present invention is compared to subjects not receiving a microorganism used in the present invention. In such comparison the concentration of glycolithocholic acid and/or taurolitocholic acid is increased in the subject receiving the microorganism used in the present invention. Alternatively or additionally, the bile acid glycolithocholic acid and/or taurolitocholic acid can be increased in subjects receiving a microorganism used in the present invention compared to the subjects before receiving a microorganism used in the present invention. Thus, also an increase similar to the latter detected increase in the concentration of glycolithocholic acid and/or taurolitocholic acid can be considered to promote gut health.

The term "subject" refers to any subject suitable for the purposes of the present invention. The subject can be a vertebrate. Thus, the subject can be a mammal, bird, amphibian, reptile or fish. Mammals include, but are not limited to, farm animals, sport animals, pets, primates, human, mice and rats. The mammal can be a human, dog, cat, mouse, rat etc. The subject can also be a horse, cow, pig, goat, chicken, sheep, donkey, rabbit, alpaca, llama, goose, ox, turkey, or the like. The subject can also be a human. The subject can be an animal, preferably the subject can be mammal. For example, the subject can be a pig, preferably a piglet, preferably a weaning piglet.

The subject can be a "healthy subject". A healthy subject may be a subject not affected by a disease or disorder. Preferably, the definition of a "healthy subject" comprises subjects which are not affected by poisoning due to toxins, which are for example present in the food or feed. Preferably, the definition of a "healthy subject" comprises subjects which are not affected by harmful gut flora. More preferred, the harmful gut flora comprises harmful bacterial flora. For example, a healthy subject can have a concentration of bile acids comparable to a control level or control value. Also the healthy subject can have a concentration of one or more bile acid(s) measured in a plasma sample, which has been obtained from the subject, which concentration of bile acids is comparable to the concentration of bile acids present in a control sample. In particular, the concentration of the bile acids GLCA and/or TLCA, when measured in a plasma sample, which has been obtained from the (healthy) subject is comparable (is about the same) as the concentration of GLCA and/or TLCA measured in a control sample. Such bile acids can be measured in a plasma sample, which has been obtained from the subject. How such bile acids are measured is known to the skilled person and also described herein.

The subject may also be a subject afflicted with a disease or disorder. Such disorders or disease can for example include diseases or disorders affecting the gut. The healthy subject can also be a weaned animal.

As used herein a "control" refers to any control suitable for the methods/uses of the present invention. For example, a control can be a concentration of a biomarker/marker e.g. the concentration of a certain bile acid as described herein determined in a control sample. Alternatively or additionally, the control may also be a control value, which has been determined by means and methods known by the skilled artesian.

For example, a control level/concentration of a biomarker/marker (e.g. bile acid) can be the concentration of the marker in a sample obtained from a healthy subject e.g. an animal not afflicted with diseases of the gut or a disease as described herein. Thus, the control sample can e.g. be obtained from a healthy subject e.g. a subject, such as an animal, not afflicted with any disease or disorder, particularly not any disease or disorder affecting the gut. Then the concentration of the marker e.g. a bile acid as described herein can be measured in this control sample to provide a control value for comparison. The subject from which the control sample can be obtained can, for example, have the same age and/or weight etc. as the subject from which the sample is obtained or which is to be tested. For example, the control or control sample can be of the same type as the sample obtained from the subject.

The control for the purposes of the present invention can also comprise healthy (control) subjects, preferably subjects, who do not have a disease or disorder, particularly not having a disease or disorder affecting the gut, or even standard controls that represent a healthy control group, or general, known in the art standards for gut disease. Subjects of the control group ideally have no concurrent disease or disorder and particularly not any gut disease. A control group can be a group of several healthy, for example, 3 or more, preferably 5 or more, more preferably 10, 20, 30, 40, or 50 persons and health can be examined with known methods, some of which are also mentioned herein.

The control may also be a weaned subject. The control may also be a subject not receiving the microorganism used in the present invention.

The present invention also relates to a method for the production of chenodeoxycholic acid (CDCA), the method comprising
a) contacting a microorganism of the class Coriobacteriia with a glycochenodeoxycholic acid (G-CDCA);
thereby obtaining chenodeoxycholic acid.

Additionally or alternatively, the present invention also relates to a method for the production of chenodeoxycholic acid (CDCA), the method comprising
a) contacting a microorganism of the class Coriobacteriia with a taurochenodeoxycholic acid (T-CDCA);
thereby obtaining chenodeoxycholic acid.

The microorgansims used in the present invention are capable to perform this deconjugation step necessary for converting T-CDCA/G-CDA into CDCA can be seen from the Examples described herein.

As used herein "chenodeoxycholic acid" (also known as chenodesoxycholic acid, chenocholic acid and 3α,7α-dihydroxy-5β-cholan-24-oic acid or CDCA) occurs as a bile acid. Salts of this carboxylic acid are called chenodeoxycholates. Chenodeoxycholic acid is one of the main bile acids produced by the liver. It is insoluble in water but soluble in alcohol and acetic acid, with melting point at 165-167° C. Chenodeoxycholic acid can be synthesized in the liver from cholesterol by a process which involves several enzymatic steps. Like other bile acids, it can be conjugated in the liver with taurine or glycine, forming taurochenodeoxycholic acid (T-CDCA) or glycochenodeoxycholic acid (G-CDCA). In particular, such conjugates are formed by a $C_{-24}$ N-acyl amide bond, which links the bile acid to its amino conjugate (glycine and taurine). However, depending on the species it may also be a $C_{-25}$ N-acyl amide bond, a $C_{-26}$ N-acyl amide bond or a $C_{-27}$ N-acyl amide bond.

Typically, hydrolysis of the $C_{-24}$ N-acyl amide bond of conjugated bile acids is catalyzed by bile salt hydrolases (BSHs). Most BSHs hydrolyze both glycine and taurine conjugated bile acids whereas a few display strong specificity. BSH genes have been detected in the main bacterial genera of the gut microbiota and the enzyme can e.g. be purified from *Bacteroides fragilis, B. vulgatus, Clostridium perfringens, Listeria monocytogenes* and several species of *Lactobacillus* and *Bifidobacterium*.

Thus, to confirm that the method of the present invention works, the following test can be performed. First a culture of microorganisms used in the present invention and a second culture comprising one of the bacteria that are able for this conversion e.g. *Clostridium perfringens*, are contacted with T-CDCA and/or G-CDCA. After an amount of time, culture supernatant is sampled and analyzed for the presence of CDCA. If CDCA is present in both cultures then the method of the present invention has been shown to work.

The method may include contacting T-CDCA and/or G-CDCA with a preparation comprising the microorganism used in the present invention. For example, the preparation may comprise only cytoplasmic components of the microorganism used in the present invention.

The method may further comprise the step of purifying chenodeoxycholic acid.

In addition, methods to perform such reactions as well as suitable buffers etc. are known to the skilled person and are also described in the Examples herein. It is further contemplated that the method is performed in a bioreactor such as a large-scale bioreactor.

The chenodeoxycholic acid obtained by a method of the present invention can be used for any purpose. For example, it can be used in a method for dissolving gallstones. Additionally or alternatively, chenodeoxycholic acid obtained by a method of the present invention can be used in the treatment of cerebrotendineous xanthomatosis, Hepatitis C infection and/or constipation.

The present invention also relates to a method for the production of lithocholic acid (LCA), the method comprising a) contacting a microorganism of the class Coriobacteriia with a chenodeoxycholic acid (CDCA)
thereby obtaining litocholic acid.

As used herein the term "lithocholic acid", also known as "3α-hydroxy-5β-cholan-24-oic acid" or "LCA", is a bile acid that acts as a detergent to solubilize fats for absorption. LCA is known to be produced from e.g. bacterial 7α-dehydroxylase from CDCA. It is known that strains of the *Clostridium* and Eubacteria can perform such 7-dehydroxylation.

For example, in hepatocytes, both primary and secondary bile acids undergo amino acid conjugation at the $C_{-24}$ (or $C_{-25}$, $C_{-26}$ or $C_{-27}$) carboxylic acid on the side chain, and almost all bile acids in the bile duct therefore exist in a glycine conjugated form. Bacterial action in the colon can produce LCA from chenodeoxycholic acid by reduction of the hydroxyl functional group at carbon-7 in the "B" ring of the steroid framework. Once produced LCA can become conjugated to glycine to form G-LCA (or GLCA as used herein). Once produced LCA can also become conjugated to taurine to form T-LCA (or TLCA as used herein).

Notably, in the in vivo Examples described herein, an increase in glycolithocholic acid and taurolitocholic acid has been found. Since lithocholic acid becomes conjugated to glycine or taurine e.g. in the hepatocytes it is clear that also an increase in lithocholic acid itself must have been present. Notably in the Examples described herein (e.g. in FIG. 2), litocholic acid has been measured and was numerally increased in group B (receiving a microorganism used in the present invention) compared to group A (not receiving a microorganism used in the present invention). Thus, although not significant nevertheless an increase of LCA form 128.7 to 155.9 nM (data not shown in the Examples) has been detected in group B. Since LCA is produced from CDCA an increase in CDCA conversion must have been present. Thus, it is also plausible that microorganism of the present invention is capable to also perform the conversion from CDCA to LCA.

The method may include contacting CDCA with an preparation as described herein comprising the microorganism used in the present invention. For example, the preparation may comprise only cytoplasmic components of the microorganism used in the present invention.

The method may further comprise the step of purifying LCA.

In addition, methods to perform such reactions as well as suitable buffers etc. are known to the skilled person and are also described in the Examples herein. It is further contemplated that the method is performed in a bioreactor such as a large-scale bioreactor.

The LCA obtained by a method of the present invention can be used for any purpose. For example the LCA may be used for treating cancer such as colon cancer or in a method for activating the vitamin D receptor.

Methods to confirm that chenodeoxycholic acid/litocholic acid is produced by the microorganism used in the present invention or that indeed T-CDCA and/or G-CDCA or LCA is utilized as substance are known to the skilled artesian. For example, commercial ELISA kits for this purpose are available. Further one method is also described in the Examples herein. Alternatively the presence of chenodeoxycholic acid/LCA can also be determined by chromatography methods also known to the skilled person.

The present invention also relates to a method for promoting gut health of a healthy subject, the method comprising a) contacting the subject with a microorganism of the class Coriobacteriia.

For the methods of the present invention what has been said for the use of the present invention applies mutatis mutandis.

The present invention also relates to a microorganism of the class Coriobacteriia for use in promoting gut health of a subject, preferably the subject is afflicted with a disease or disorder. The microorganism of the class Coriobacteriia can also be used for treating a subject that is afflicted with a disease or disorder as described herein.

The microorganism of the class Coriobacteriia can also be used for preparing a composition for treatment of a subject that is afflicted with a disease or disorder as described herein. The composition may comprise further ingredients as described herein for the composition for promoting gut health of a healthy subject.

As used herein the term "treating" or "treatment" can include administration of a microorganism as used in the present invention preferably in the form of a medicament, e.g. to a subject suffering from a disease affecting the gut for the purpose of ameliorating or improving symptoms.

The subject may be affected by any disease e.g. disease of the gut. Exemplary diseases include sepsis, diarrhoea, inflammatory bowel disease, irritable bowel disease, obesity, diabetes, liver diseases, chronic heart diseases, celiac disease and cancers.

The subject may be affected by a disease of the immune system.

The present invention also relates to a method for the production of chenodeoxycholic acid (COCA), the method comprising
a) contacting a microorganism of the class Coriobacteriia with a tauro- and/or glycochenodeoxycholic acid (G-CDCA);
thereby obtaining chenodeoxycholic acid.

The present invention also relates to a method for promoting gut health of a healthy subject, the method comprising
a) contacting the subject with a microorganism of the class Coriobacteriia.

The present invention also relates to a kit comprising the microorganism used in the present invention. The kit may further comprise a prebiotic and/or a probiotic. For example the kit may comprise at least one microorganism different from the microorganism used in the present invention. For example, the microorganism different from the microorganism used in the present invention can be selected from *Clostridium* e.g. *Clostridium perfringens*, Eubacteria, *Bacteroides fragilis*, *B. vulgatus*, *Listeria monocytogenes*, *Lactobacillus* and *Bifidobacterium*.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, f.e. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

The following sequences are used in the present application.

| Sequence # | Description of sequence | Sequence |
|---|---|---|
| 1 | 16S-RNA sequence of DSM11798 | CCTGGCTCAGGATGAACGCTGGCGGCGTGCTTAACACA TGCAAGTCGAACGGATAACCCGCCTCCGGGCGGTTATA GAGTGGCGAACGGGTGAGTAACACGTGACCAACCTACC TCCCACTCCGGGATAACCCAGGGAAACCTGCGCTAATA CCGGATACTCCGGGGCCCCCGCATGGGGGCGCCGGG AAAGCCCCGACGGTGGGAGATGGGGTCGCGGCCTATT AGGTAGTCGGCGGGGTAACGGCCCACCGAGCCCGCGA TAGGTAGCCGGGTTGAGAGACCGATCGGCCACATTGG GACTGAGATACGGCCCAGACTCCTACGGGAGGCAGCA GTGGGGAATTTTGCGCAATGGGGGAAACCCTGACGCAG CAACGCCGCGTGCGGGACGAAGGCCTTCGGGTTGTAA ACCGCTTTCAGCAGGGAAGAAGTTGACGGTACCTGCAG AAGAAGCTCCGGCTAACTACGTGCCAGCAGCCGCGGTA |

| Sequence # | Description of sequence | Sequence |
|---|---|---|
| | | ATACGTAGGGAGCGAGCGTTATCCGGATTTATTGGGCG<br>TAAAGCGCGCGTAGGCGGGCGCTTAAGCGGAATCTCTA<br>ATCTGAGGGCTCAACCCCCAGCCGGATTCCGAACTGGG<br>CGCCTCGAGTTCGGTAGAGGAAGACGGAATTCCCAGTG<br>TAGCGGTGAAATGCGCAGATATTGGGAAGAACACCGAT<br>GGCGAAGGCAGTCTTCTGGGCCGTAACTGACGCTGAG<br>GTGCGAAAGCTAGGGGAGCGAACAGGATTAGATACCCT<br>GGTAGTCCTAGCCGTAAACGATGGGCACTAGGTGTGGG<br>GGGGAATGCCCCTCCGTGCCGCAGCTAACGCATTAAGT<br>GCCCCGCCTGGGGAGTACGGCCGCAAGGCTAAAACTC<br>AAAGGAATTGACGGGGCCCGCACAAGCAGCGGAGCA<br>TGTGGCTTAATTCGAAGCAACGCGAAGAACCTTACCAG<br>GGCTTGACATGCAGGTGAAGCGGCGGAAACGCCGTGG<br>CCGAGAGGAGCCTGCACAGGTGGTGCATGGCTGTCGT<br>CAGCTCGTGTCGTGAGATGTTGGGTTAAGTCCCGCAAC<br>GAGCGCAACCCCTGTCGTATGTTGCCATCATTCAGTTG<br>GGGACTCGTACGAGACTGCCGGCGTCAAGCCGGAGGA<br>AGGTGGGGACGACGTCAAGTCATCATGCCCTTTATGCC<br>CTGGGCTGCACACGTGCTACAATGGCCGGTACAACGG<br>GCTGCGAGCCAGCGATGGCGAGCGAATCCCTCAAAAC<br>CGGTCCCAGTTCGGATCGGAGGCTGCAACCCGCCTCC<br>GTGAAGTCGGAGTTGCTAGTAATCGCGGATCAGCATGC<br>CGCGGTGAATACGTTCCCGGGCCTTGTACACACCGCCC<br>GTCACACCACCCGAGTTGTCTGCACCCGAAGTCGACGG<br>CCCAACCCGCGAGGGGGAGTCGCCGAAGGTGTGGG<br>GAGTAAGGGGGGTGAAGTCGTAACAAGGTAGCCGTACC<br>GGAAGGTGCGGCT |
| 2 | cpn60 gene (alternative name GroEL) >fig\|84107.3.peg.158 [Coriobacteriaceae] [Heat shock protein 60 family chaperone GroEL] | atggcaaaagatatcaagttcgaagccgacgcgcgcagcgctcttgcggctgga<br>gtttcaaagctggccgacgccgttaaagtgacgcttggccccaagggtcgttacgt<br>cgctctcgagaaatcctacggcgcccccaccatcaccaacgacggcgtcaccgt<br>tgccaaagaagtcgagctcgaggatccggtagagaacatgggcgcccagctcg<br>tccgcgaggttgccgttaagaccaacgatgttgcgggcgacggcaccaccaccg<br>caacgctgctcgccgacgtcatcgtctccgagggtctgcgcaacgtcaccgcagg<br>cgccgatgcgctcggcatccgccgcggcatccagaaggccaccgatgcggtggt<br>cgaagagatcaagaacaccgcaaccgaggtttccggcaaagagcagatcgcc<br>aatgtcggcaccatttccgcaggcgatgccgagatcggcgagaagatcgccgag<br>gccatggacgccgttggcaaagacggtgcgatttctgttgaggagagccagacgt<br>tcggtctcgagatggacatcgtcgagggcatgcagtacgagcgcggctacatctc<br>cccgtacatggcaaccgacatggagaagatggaagccgtcctcaaagatcccta<br>catcctccttaccgaccagaaggtcaacaacatccaggacatggttccgctgcttg<br>aagaggttatgaagtccggtcgtccgctgttcctcgtcgccgaagacgtcgagggc<br>gaggcgctcgccaccatcctgctcaacaagctgcgcggcaccttcaactgcgtcg<br>ccatcaaggccccggcttcggcgatcgtcgcaagcgcatcctcgaggacattgc<br>ggccgttaccggcgcgcaggtcatcgacaaggacttcggcatgaccatggccga<br>tgccaccatcgatatgatgggccacgcgaagaccgtcaaggtcaccaaggaca<br>gcgcgctcatcgttgacggcgcaggcgataagaaggccatcgaggatcgcatcc<br>atcagatcaaggccgagctcgaccgcgtcgactccgacttcgatcgcgagaagc<br>tccaggagcgcttggccaagctctccggcggcgttgcggtgctcaaggtgggcgc<br>tgctaccgaatcggagctcaaggaaaagaagagccgcattgaagatgcgctgc<br>aggcaacccgcgcagcggtcgaagagggcatcgttgccggcggcggcgtggc<br>gcttgtgaacgctatcccccgcactcgacaaggttgaagtcgccgacaaggacga<br>agaggtcggcgtgagcatcgtccgcaaggcgcttgaggctcccatgcgcgccatt<br>gctcaaaacgccggtttcgagggaagcgtcgttgtcgagcacgtgaagggcatg<br>aaggtcggcgaaggcctgaactgcgctacgggcgagtatggcaacatgatcga<br>gatgggcgtgaacgatccggtgaaggttacccgtacggcgctgcagtctgccgctt<br>ccgtgggtgcgctcatcctcatcaccgaagccacgatcaacgagatcccgaaag<br>agggccccgacttgtctgcgctcgccggtgctggcggcatgggcgggatgatgtag |

A better understanding of the present invention and of its advantages will be had from the following examples, offered for illustrative purposes only. The examples are not intended to limit the scope of the present invention in any way.

EXAMPLES OF THE INVENTION

Example 1: G-CDCA De-Conjugation by BBSH 797

Buffer solutions used in the Example:

mineral solution I: $K_2HPO_4$ (6 g/L), $KH_2PO_4$ (6 g/L), $(NH_4)_2SO_4$ (6 g/L), NaCl (12 g/L), $H_2O$ dist. add to 1 L mineral solution II: $MgSO_4 \times 7$ $H_2O$ (2.5 g/L), $H_2O$ dist. add to 1 L mineral solution III: $CaCl_2 \times 2$ $H_2O$ (3 g/L), $H_2O$ dist. add to 1 L vitamin solution: Biotin (Vitamin H, 2 mg/L), Folic acid (2 mg/L), Pyridoxine-HCl (Vitamin B6, 10 mg/L), Thiamin-HCl (Vitamin B1, 5 mg/L), Riboflavin (Vitamin B2, 5 mg/L), Nicotinamide (5 mg/L), D,L-Pantotheinate (5 mg/L), Cyanocobalamin (Vitamin B12, 0.1 mg/L), Menadione (100 mg/L), Phyllochinon (Vitamin K1, 22 mg/L), p-Aminobenzoic acid (5 mg/L), Thioctic acid (5 mg/L), $H_2O$ dist. add to 1 L; stored at 4° C.

trace element solution (TE): $ZnSO_4 \times 7$ $H_2O$ (0.10 g/L), $MnCl_2 \times 7$ $H_2O$ (0.03 g/L), $H_3BO_3$ (0.30 g/L), $CuCl_2 \times 2$ $H_2O$ (0.01 g/L), $CoCl_2 \times 6\ H_2O$ (0.20 g/L), $NiCl_2 \times 6\ H_2O$ (0.02 g/L), $Na_2MoO_4 \times 2\ H_2O$ (0.03 g/L), $H_2O$ dist. Add to 1 L; stored at 4° C.

hemin solution (10 000 ppm): 1 g hemin was dissolved in 50 ml 1 M NaOH solution. Afterwards 50 ml EtOH (92.7% v/v) was added. Stored at 4° C.

phosphate buffer: 0.5 M $KH_2PO_4$ Puffer+0.5 M $Na_2HPO_4 \times 2\ H_2O$, pH=6.9, sterile filtrated cystein-$Na_2S$ solution (reducing agent): The solution is made under $N_2$-atmosphere in a Schott flask with septum cap. 0.5 g Cystein-HCl were dissolved in 18.2 ml cooked, $N_2$-aerated distilled water. 1.8 ml 4 M NaOH (pH 10) and 0.5 g $Na_2S$ were added. Prepared freshly, sterile filtrated and stored at 4° C.

dilution buffer: Combine 75 ml mineral solution I, II and III each with 10 ml vitamin solution, 0.5 ml trace element solution, 0.5 ml hemin solution and 0.5 g cystein-HCl; $H_2O$ dist. add to 1 L. pH=6.8 to 6.9 (adjusted with 4 M NaOH solution), autoclaved at 121° C. for 15 minutes, prepared freshly!

To determine the ability of BBSH 797 to de-conjugate GCDCA into CDCA incubation experiments have been performed. Therefore, the following three types of batches were generated in triplicates:

Batch T containing GCDCA and BBSH 797 (4.09E+6 CFU/mL)

Batch C1 containing GCDCA only without BBSH 797

Batch C2 containing GCDCA together with inactivated BBSH 797 (4.09E+6 CFU/mL).

Inactivated BBSH 797 means that the BBSH 797 is not viable.

Sampling was done at t=0 and after 48 hours of incubation

In detail the following procedure was performed:

The dilution buffer was sterile filtrated and 2.5% (v/v) phosphate buffer and 1% (v/v) reducing agent were added to obtain the final dilution buffer. 18 ml final dilution buffer were placed into sterile 25 ml Schott flasks for all of the treatment experiments (T batches) and the inactivation controls (C2 batches). 20 mL final dilution buffer were placed into sterile 25 mL Schott flasks for negative control (C1 batches). 200 µL of a GCDCA solution was added to all batches to obtain a final concentration of 5 µM.

The BBSH 797 culture was grown from lyophilisates and a BBSH 797 inoculum (4.09E+7 CFU/mL) was prepared in final dilution buffer. 2 mL from this inoculum were added into the T batches to obtain 20 mL (volume of GDCA solution neglected) having a cell density of 4.09E+6 CFU BBSH 797 per mL. A part of the BBSH 797 inoculum (4.09E+7 CFU/mL) was inactivated by incubating it in a water bath at 90° C. for 15 min. 2 mL from this inactivated inoculum were added into the C2 batches to obtain 20 mL (volume of GDCA solution neglected) having a cell density equivalent to 4.09E+6 CFU inactivated BBSH 797 per mL.

At time t=0 minutes, all batches were homogenized by shaking and samples (t0 samples, 1 mL) were taken that were immediately heated to 95° C. for 5 minutes and stored at −20° C.

All batches were further incubated at 37° C. for 48 hours. After 48 hrs all batches were homogenized by shaking and samples (t=48 h samples, 1 mL) were taken that were immediately heated to 95° C. for 5 minutes and stored at −20° C. Before quantification of GCDCA and CDCA all samples were thawed and centrifuged at 16,600×g for 10 minutes. 10 µl of the cleared samples were diluted with 990 µL of the HPLC eluent (20% acetonitrile+80% dist. $H_2O$) and the GCDA and CDCA amounts were quantified.

Figure 1:
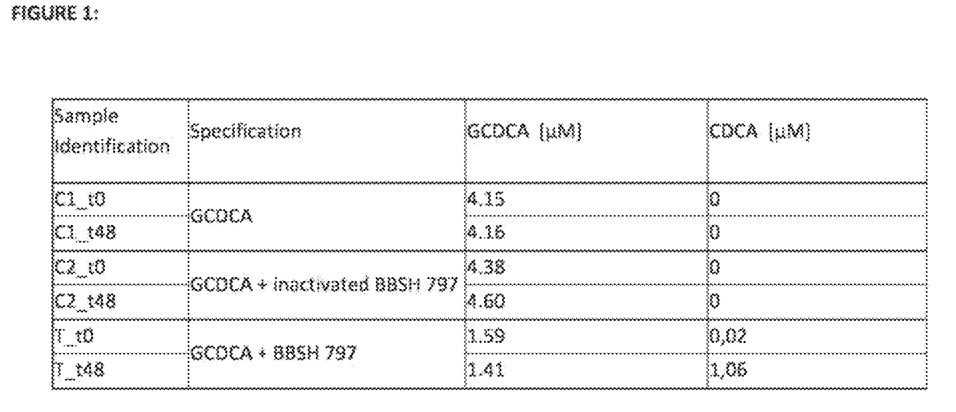
FIG. 1 is a table of results obtained in the in vitro experiment showing a conversion of glycochenodeoxycholic acid to chenodeoxycholic acid.

The results obtained are summarized in FIG. 1. What can be seen from FIG. 1 is that in both control batches (C1 and C2) no transformation of GCDCA into CDCA was identified. Therefore, GCDCA is not de-conjugated spontaneously (C1) neither by inactivated (dead) BBSH 797 microorganism. For the treatment (T-batches) it is clearly shown that GCCA is taken up by the living microorganism very fast as the t=0 h samples already show significantly reduced GCDCA concentrations in the incubation medium (1.59 µM) compared to C1 and C2 samples. Furthermore, GCDCA is de-conjugated by living BBSH 797 and CDCA is generated (0.02 µM CDCA at t=0 h and 1.06 µM CDCA at t=48 h). A reason why not more GCDCA and CDCA was found in the incubation buffer of the T-batches may be due to an intermediate storage of both substances within the microorganism.

Thus, only active BBSH 797 is capable of converting GCDCA into CDCA. From these data it can be concluded that BBSH 797 is able to hydrolyse the $C_{24}$ N-acyl amide bond (and therefore probably also the $C_{25}$ N-acyl amide bond, the $C_{26}$ N-acyl amide bond and $C_{27}$ N-acyl amide bond) of conjugated bile acids. Therefore it can be expected that BBSH 797 comprises one or more enzymes which can perform this hydrolysis. It can also be expected that also taurine conjugated CDCA can become hydrolased in the presence of BBSH 797.

In summary, in vitro experiments showed a conversion of glycochenodeoxycholic acid to chenodeoxycholic acid. According to the literature, the latter leads to a release of GLP-2 and thus to improved intestinal integrity (Diego-Cabero et al., 2015). Based on the in vitro experiments, an in vivo study was conducted with weaned piglets to evaluate the effect of BBSH 797 on the intestinal barrier.

Example 2: Feeding Experiments

Experimental Setup

A total of 16 piglets (Ö-HYB, 4-5 weeks old, about 10 kg) were divided into two different groups after weaning. Group A received a feed composition (complete weaning feed), whose components were adapted to the age of the animals. In group B BBSH 797 was added to the same weaning feed (final feed concentration of BBSH 797 of $2.2*10^9$ colony forming units/tkg of weaning feed composition). Over the trial period of 44 days, the feed was given twice a day. The piglets had free access to drinking water, were kept under controlled conditions (space, temperature, humidity and light) and received piglet toys as enrichment. The animals were looked after daily by trained persons and supervised by veterinarians.

Sampling:

On day 42, individual blood samples were taken from the cava cranial vein of all animals (Primavette® EDTA, Kabe Laboratory GmbH, Nuembrecht-Elsenroth, Germany). After centrifuging (2.300×g, 10 min), two aliquots (100 µL each) were transported on dry ice to Biocrates Life Sciences AG (Innsbruck, Austria). There, the samples were stored at −80° C. until bile acid concentrations were determined.

On day 42 and 43, the piglets were kept in metabolic cages. On these two days, around 9 am, the animals were given approximately 15 ml of agar agar containing lactulose (500 mg/kg body weight) and rhamnose (100 mg/kg body weight). Subsequently, urine was collected for each of three different time periods: 0-2, 2-4 and 4-6 hours after administration of the sugar solution. In addition, a urine sample was collected directly before the first sugar administration (blank sample). The urine samples were stored at −20° C. until analysis of the lactulose/rhamnose ratio.

Analysis of Samples:

For the measurement of bile acids, a commercially available Bile Acid Test Kit (Biocrates Life Sciences AG, Innsbruck, Austria) was used. For this purpose, the samples were extracted by means of the dried filter spot technique and then analyzed by means of liquid chromatography tandem mass spectrometry (Thermo Fischer Scientific TSQ, negative electrospray ionization, multiple reaction monitoring mode). A total of 20 primary and secondary bile acids were quantified using external (7-point calibration curve) and internal standards (10 isotope-labeled standards). The data was then evaluated using Thermo Fischer Scientic Xcalibur™ and Biocrates MetIDQ software.

Figure 2:
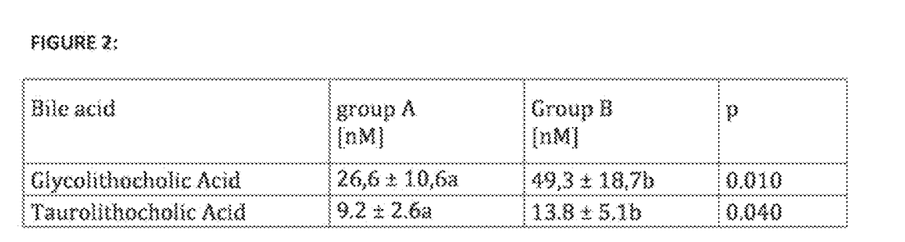
FIG. 2 is a table of results showing the effect of BBSH 797 on the plasma concentration of bile acids (mean±standard deviation, day 42) in weaned piglets. The animals (n=8) received either weaning feed (Group A) or weaning feed with addition of BSH 797 (2.2*10$^9$ colony forming units/kg feed, Group B) for 42 days. Statistically significant differences ($p<0.05$) between the two groups are indicated by superscripts (a, b).

Results and Discussion:

On day 42, a significant increase in bile acids glycolithocholic acid and taurolithocholic acid was observed in group B (FIG. 2). They represent secondary bile acids, to which an amino acid (glycine or taurine) is bound. In general, conversion of primary (cholic acid, cenodeoxyholic acid) to secondary bile acids (deoxycholic acid, lithocholic acid) occurs through intestinal microbes. Thus, the necessary enzymatic metabolic processes (deconjugation, 7-hydroxylation) in various bacterial genera such as *Bacteroides*, *Bifidobacterium* or *Clostridium* have been described (Gerard, 2014). For BBSH 797 (genus novus from the family Coriobacteriaceae, strain number DSM 11798), no such reports are available so far.

For the measurement of lactulose and rhamnose, urine was diluted by a factor of $1.6*10^6$ over several intermediate steps with methanol. Subsequently, lactulose and rhamnose were determined by an LC-MS method. For this, an Agilent 1290 Infinity I instrument (Agilent Technologies, United States) to which a Triple Quad 5500 mass spectrometer (AB Sciex, Canada) was coupled was used. The analytes were separated on a Luna NH2 150×2.0 mm column (Phenomenex, United Kingdom, 30° C., 0.250 mL/min, acetonitrile gradient elution for 10 min). The mass spectrometer was operated with negative electrospray ionization and in multiple reaction monitoring mode (m/z 341→m/z 161 and m/z 341→m/z 101 for lactulose; m/z 163→m/z 59 and m/z 163→m/z 103 for rhamnose). The data were analyzed using Analyst Software (AB Sciex, Canada) and the lactuolose/rhamnose ratio calculated in MS-Excel (Microsoft, USA).

Figure 3:
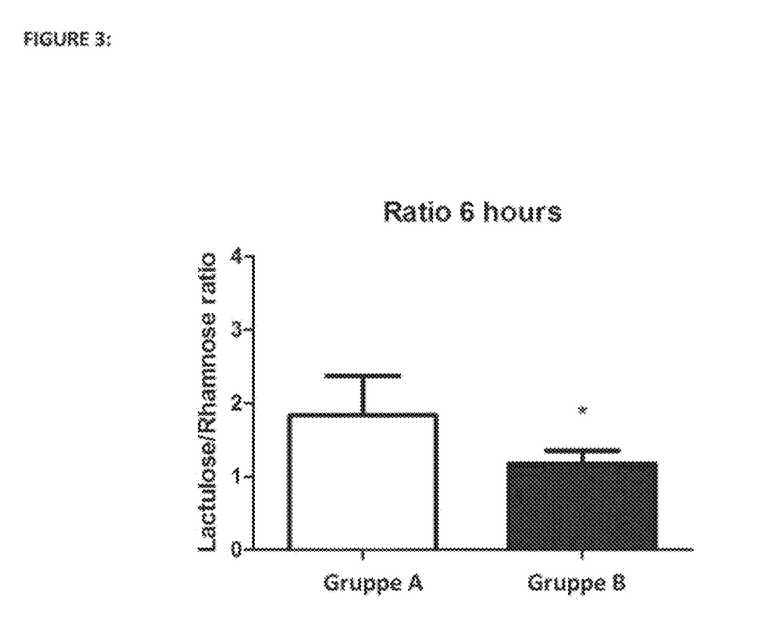
FIG. 3 is a graph showing the influence of BBSH 797 on the lactulose/rhamnose ratio in the weaned pig urine six hours after administration of a sugar solution (500 mg lactose/kg body weight, 100 mg rhamnose/kg body weight, day 43). Animals (n=8) received either weaning feed (Group A) or weaning feed with addition of BBSH 797 ($2.2*10^9$ colony forming units/kg feed, Group B) for 44 days. The statistically significant difference $p<0.05$) between the two groups is indicated by a superscript (*).

In the experiment, a correlation between elevated bile acid concentrations and an improved intestinal barrier could be demonstrated. The integrity of the intestinal barrier was assessed using a dual-sugar assay. The principle of this test is based on co-administration of lactulose and rhamnose. The disaccharide lactulose enter the bloodstream only paracellularly through the narrow gaps between the individual intestinal epithelial cells. On the other hand, the monosaccharid rhamnose are transported into the body both paracellularly and transcellularly through the intestinal cells. When the intestinal barrier weakens, the interstitial space becomes increasingly porous, as a result of which comparatively larger amounts of disaccharides are absorbed. Consequently, the lactulose/rhamnose ratio in the urine increases. An intact or strengthened intestinal barrier is associated with a reduced lactulose/rhamnose ratio in the urine (Wijtten et al., 2011 cited herein). In the performed experiment, administration of BBSH 797 for several weeks resulted in a significantly reduced urinary lactulose/rhamnose ratio (p=0.0173, FIG. 3).

Example 3: Effect of BBSH 797 on Weight Gain and Feed Conversion Rate (FCR) in Healthy Subjects Experimental Setup Mixed sexed weaning piglets (Genetic type: 0-HYB FI [(Landrace×Large White)×Pietrain]) of approximately 4-10 weeks of age were ear-tagged, individually weighed and assigned to either a control group (CG), a trial group (TG) or a high-concentration trial group (hTG). The animals were selected out of a healthy herd. Animals of the control group (CG) were fed a basal diet containing no antibiotics, coccidiostats, probiotics, phytogenic additives or organic acids. The basal diet feed contained the following ingredients for days 1-14 in % (w/w): Corn, 30; barley, 32.9; sunflower oil, 0.6; potato protein, 7; maize pressure cooked, 6; soya protein concentrate, 5.7; wheat pressure cooked, 4; dextrose, 4; lactose, 3; palm kernel, cocos fat, 2.5; mono calcium phosphate, 1.23; magnesium phosphate, 0.1; sodium chloride, 0.43; vitamin premix, 0.1; trace element premix, 0.15; L-lysine, 0.56; DL-methionine, 0.17; L-threonine, 0.16; L-tryptophane, 0.08; sweetener, 0.02. For days 15-42, the basal diet feed contained the following ingredients in % (w/w): Corn, 40.7; barley, 35; soya 48%, 20; sunflower oil, 0.5; mono calcium phosphate, 0.94; calcium carbonate, 1.31; magnesium phosphate, 0.2; sodium chloride, 0.46; vitamin premix, 0.1; trace element premix, 0.15; L-lysine, 0.4; DL-methionine, 0.12; L-threonine, 0.12. Animals of the trial group (TG) were fed the same basal diet as the control group but the feed was additionally supplemented with BBSH 797 (DSM 11798) to a final concentration of $2.2*10^9$ CFU per kg of feed. Animals of the high-concentration trial group (hTG) were also fed the same basal diet as the CG but the feed was additionally supplemented with BBSH 797 (DSM 11798) to a final concentration of $2.2*10^{11}$ CFU per kg of feed. The treatment period was 42 days. During the whole trial period, the animals were fed ad libitum. Fresh drinking water was supplied ad libitum as well. Climatic conditions were computer-operated, regulated automatically according to the standard recommendations for weaning piglets and recorded daily. In the morning and in the afternoon, the farm staff checked the general health status of the animals and controlled the housing facilities to ensure constant feed and water supply, correct temperature and ventilation. In addition, the animals were examined regularly by a veterinarian to confirm the good health of the animals throughout the trial. During the trial, feed intake was accurately measured per pen. Body weight was individually determined on days 1, 14 and 42. Average daily feed intake per pen was determined between days 1 and 42 as well as between days 15 and 42. Average feed intake and average body weight per pen were used to calculated the average feed to weight gain ratio (feed conversion rate, FCR).

Results:

Throughout the whole trial period all animals remained free of any perceivable health problems or any symptoms of clinical diseases and no losses occurred. The beneficial effect of feed supplementation with BBSH 797 on weight gain is shown in the following table 1.

TABLE 1

Effect of feed-supplementation with BBSH 797 on weight gain in healthy animals.

| | Average daily weight gain (g) | | |
| --- | --- | --- | --- |
| | CG | TG | hTG |
| Day 1-42 | 470 | 492 | 487 |
| Day 15-42 | 581 | 614 | 594 |

Also the feed to weight gain ratio, also referred to as the feed conversion rate (FCR), was found improved in animals fed a BBSH 797-supplemented basal diet over animals fed solely basal diet not supplemented with BBSH 797. In the period of day 1-42, the FCR improved from 1.63 kg/kg of the animals fed solely basal diet to 1.54 kg/kg of the animals fed BBSH 797-supplemented basal diet. In the period of day 15-42, the FCR improved from 1.69 kg/kg of the animals fed solely basal diet to 1.59 kg/kg of the animals fed BBSH 797-supplemented basal diet. As shown in the Examples herein, feed supplementation with BBSH 797 promoted the gut health of healthy animals, resulting in an improvement of both, weight gain and feed conversion rate of animals fed BBSH 797-supplemented feed, while no adverse effects were observed.

LIST OF REFERENCES

Altschul Nucl. Acids Res. 25 (1977), 3389-3402
Altschul, J. Mol. Biol. 215 (1990), 403-410
Altschul, J. Mol. Evol. 36 (1993), 290-300
Altschul, Nucl. Acids Res. 25 (1997), 3389-3402
Boesjes and Brufau (2014) "Metabolic effects of bile acids in the gut in health and disease" Current Medicinal Chemistry, 21, 2822-2829
Brutlag Comp. App. Biosci. 6 (1990), 237-245
Connor et al. (2016) "Glucagon-like peptide 2 and its benefcial effects on gut function and health in production animals" Domestic Animal Endocrinology 56 S56-S65
de Diego-Cabero et al. (2015) "Bile acid mediated effects on gut integrity and performance of early-weaned piglets." BMC veterinary research 11:111
Derikx et al. (2010) "Non-invasive markers of gut wall integrity in health and disease" World Journal of Gastrology 16(42):5272-5279
Grootjans et al. (2010) "Non-invasive assessment of barrier integrity and function of the human gut" World J Gastrointest Surg; 2(3): 61-69
Gupta et al. (2013) "Molecular signatures for the class Coriobacteriia and its different clades; proposal for division of the class Coriobacteriia into the emended order Coriobacteriales, containing the emended family Coriobacteriaceae and Atopobiaceae fam. nov., and Eggerthellales ord. nov., containing the family Eggerthellaceae fam. nov." Int. J. Syst. Evol. Microbiol. 63 (Pt 9), pp. 3379-3397
Henikoff Proc. Natl. Acad. Sci., USA, 89, (1989), 10915
Hofmann et al. (1992) "A proposed nomenclature for bile acids" Lipid Res. 1992 April; 33(4):599-604
Kawamata et al. (2003) "A G protein-coupled receptor responsive to bile acids*" vol. 278, no. 11, pp. 9435-9440
Matsuki et al. (2004) Use of 16S rRNA Gene-Targeted Group-Specific Primers for Real-Time PCR Analysis of Predominant Bacteria in Human Feces. *Applied and Environmental Microbiology* 70(12): 7220-7228).
Slavin (2013) "Fiber and Prebiotics: Mechanisms and Health Benefits" Nutrients. 5(4): 1417-1435
Thompson Nucl. Acids Res. 2 (1994), 4673-4680
Torres et al. (2010) "Galacto-Oligosaccharides: Production, Properties, Applications, and Significance as Prebiotics" Comprehensive Reviews in Food Science and Food Safety, Volume 9, Issue 5, p. 438-454
Schaap et al. (2014) "Bile acid receptors as targets for drug development" Nature Reviews Gastroenterology & Hepatology 11(1):55-67
Wang et al. (2015) "Methods to determine intestinal permeability and bacterial translocation during liver disease." J Immunol Methods; 421: 44-53.
Wijtten et al., (2011) "Intestinal barrier function and absorption in pigs after weaning: a review." Br J Nutr 105:967-981

The invention claimed is:

1. A method of increasing the bile acid(s) glycolithocholic acid (GLCA) and/or taurolitocholic acid (TLCA) within a subject compared to GCLA and/or TLCA present before administration of the microorganism comprising administering to a healthy subject a microorganism of the class Coriobacteriia and the order Eggerthellales, wherein the microorganism is provided within a food and/or feed composition, wherein administering causes an increase in GLCA and/or TLCA within the subject, and wherein the food- and/or feed composition without the microorganism therein, when administered to the subject, does not have a toxic effect on the subject.

2. The method of claim 1, wherein the microorganism is a microorganism of the strain DSM11798.

3. The method of claim 1, wherein both GLCA and TLCA are increased in the subject.

4. The method of claim 3, wherein GLCA is increased to a greater extent than TLCA is increased.

5. The method of claim 1, wherein the microorganism is provided for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, or 70 or more days, optionally wherein the microorganism is provided for a time in the range of 42 or 44 days.

6. The method of claim 5, wherein the microorganism is provided for 14 or more days, or 21 or more days.

7. The method of claim 1, wherein the microorganism is provided in a dosage of $0.25 \times 10^9$, $0.5 \times 10^9$, $0.75 \times 10^9$, $1.0 \times 10^9$, $1.25 \times 10^9$, $1.5 \times 10^9$, $1.75 \times 10^9$, $2.0 \times 10^9$, $2.25 \times 10^9$, $2.5 \times 10^9$, $2.75 \times 10^9$, $3.0 \times 10^9$, $3.25 \times 10^9$, $3.5 \times 10^9$, $3.75 \times 10^9$, $1.0 \times 10^9$, $1.25 \times 10^9$, $1.5 \times 10^9$, $1.75 \times 10^9$, $4.0 \times 10^9$ or more colony forming units (CFU) per kg of the food- and/or feed composition, optionally wherein the microorganism is provided in a dosage of at least $2.2 \times 10^9$ colony forming units per kg composition.

8. The method of claim 1, wherein the microorganism converts glycochenodeoxycholic acid (G-CDCA) into chenodeoxycholic acid (CDCA).

9. The method of claim 1, wherein the healthy subject is a subject not affected by a disease or disorder.

10. The method of claim 1, wherein the healthy subject has a concentration of bile acids measured in a plasma sample, which has been obtained from the subject, which concentration of bile acids is comparable to the concentration of bile acids present in a control sample.

11. A method of promoting intestinal integrity of a healthy subject, comprising administering to the healthy subject a microorganism of the class Coriobacteriia and the order Eggerthellales, wherein administering causes intestinal integrity which is, in the least, characterized by a test which feeds lactulose and rhamnose to the subject, measures a lactulose/rhamnose ratio in urine 6 hours after feeding, and determines said lactulose/rhamnose ratio is lower than a lactulose/rhamnose ratio in urine at the time point of feeding, and wherein the food- and/or feed composition without the microorganism therein, when administered to the subject, does not have a toxic effect on the subject.

12. The method of claim 11, wherein the microorganism is a microorganism of the strain DSM11798.

13. The method of claim 11, wherein the microorganism is provided in a dosage of $0.25 \times 10^9$, $0.5 \times 10^9$, $0.75 \times 10^9$, $1.0 \times 10^9$, $1.25 \times 10^9$, $1.5 \times 10^9$, $1.75 \times 10^9$, $2.0 \times 10^9$, $2.25 \times 10^9$, $2.5 \times 10^9$, $2.75 \times 10^9$, $3.0 \times 10^9$, $3.25 \times 10^9$, $3.5 \times 10^9$, $3.75 \times 10^9$, $1.0 \times 10^9$, $1.25 \times 10^9$, $1.5 \times 10^9$, $1.75 \times 10^9$, $4.0 \times 10^9$ or more colony forming units (CFU) per kg of the food- and/or feed composition, optionally wherein the microorganism is provided in a dosage of at least $2.2 \times 10^9$ colony forming units per kg composition.

14. The method of claim 11, wherein the microorganism is provided for 14 or more days, or 21 or more days.

* * * * *

SEQUENCE LISTING

```
<160> NUMBER OF SEQ ID NOS: 2

<210> SEQ ID NO 1
<211> LENGTH: 1477
<212> TYPE: DNA
<213> ORGANISM: Unknown
<220> FEATURE:
<223> OTHER INFORMATION: 16S-RNA sequence of DSM11798

<400> SEQUENCE: 1
cctggctcag gatgaacgct ggcggcgtgc ttaacacatg caagtcgaac ggataacccg      60
cctccgggcg gttatagagt ggcgaacggg tgagtaacac gtgaccaacc tacctcccac     120
tccgggataa cccaggaaa cctgcgctaa taccggatac tccggggccc ccgcatgggg     180
gcgccgggaa agccccgacg gtgggagatg gggtcgcggc ctattaggta gtcggcgggg     240
taacggccca ccgagcccgc gataggtagc cgggttgaga gaccgatcgg ccacattggg     300
actgagatac ggcccagact cctacgggag gcagcagtgg ggaattttgc gcaatggggg     360
aaaccctgac gcagcaacgc cgcgtgcggg acgaaggcct tcgggttgta aaccgctttc     420
agcagggaag aagttgacgg tacctgcaga agaagctccg gctaactacg tgccagcagc     480
cgcggtaata cgtagggagc gagcgttatc cggatttatt gggcgtaaag cgcgcgtagg     540
cgggcgctta agcggaatct ctaatctgag ggctcaaccc ccagccggat tccgaactgg     600
gcgcctcgag ttcggtagag gaagacggaa ttcccagtgt agcggtgaaa tgcgcagata     660
ttgggaagaa caccgatggc gaaggcagtc ttctgggccg taactgacgc tgaggtgcga     720
```

```
aagctagggg agcgaacagg attagatacc ctggtagtcc tagccgtaaa cgatgggcac      780
taggtgtggg ggggaatgcc cctccgtgcc gcagctaacg cattaagtgc cccgcctggg      840
gagtacggcc gcaaggctaa aactcaaagg aattgacggg ggcccgcaca agcagcggag      900
catgtggctt aattcgaagc aacgcgaaga accttaccag ggcttgacat gcaggtgaag      960
cggcggaaac gccgtggccg agaggagcct gcacaggtgg tgcatggctg tcgtcagctc     1020
gtgtcgtgag atgttgggtt aagtcccgca acgagcgcaa ccctgtcgt atgttgccat      1080 cattcagttg gggactcgta cgagactgcc ggcgtcaagc cggaggaagg tggggacgac     1140
gtcaagtcat catgcccttt atgccctggg ctgcacacgt gctacaatgg ccggtacaac     1200
gggctgcgag ccagcgatgg cgagcgaatc cctcaaaacc ggtcccagtt cggatcggag     1260
gctgcaaccc gcctccgtga agtcggagtt gctagtaatc gcggatcagc atgccgcggt     1320
gaatacgttc ccgggccttg tacacaccgc ccgtcacacc cccgagttg tctgcacccg      1380 aagtcgacgg cccaacccgc agggggggag tcgccgaagg tgtggggagt aaggggggtg     1440
aagtcgtaac aaggtagccg taccggaagg tgcggct                              1477
```

<210> SEQ ID NO 2
<211> LENGTH: 1629
<212> TYPE: DNA
<213> ORGANISM: Unknown
<220> FEATURE:
<223> OTHER INFORMATION: cpn60 gene

<400> SEQUENCE: 2

```
atggcaaaag atatcaagtt cgaagccgac gcgcgcagcg ctcttgcggc tggagtttca       60
aagctggccg acgccgttaa agtgacgctt ggccccaagg gtcgttacgt cgctctcgag      120
aaatcctacg gcgcccccac catcaccaac gacggcgtca ccgttgccaa agaagtcgag      180
ctcgaggatc cggtagagaa catgggcgcc cagctcgtcc gcgaggttgc cgttaagacc      240
aacgatgttg cggcgacgg caccaccacc gcaacgctgc tcgccgacgt catcgtctcc      300
gagggtctgc gcaacgtcac cgcaggcgcc gatgcgctcg gcatccgccg cggcatccag      360
aaggccaccg atgcggtggt cgaagagatc aagaacaccg caaccgaggt ttccggcaaa      420
gagcagatcg ccaatgtcgg caccatttcc gcaggcgatg ccgagatcgg cgagaagatc      480
gccgaggcca tggacgccgt tggcaaagac ggtgcgattt ctgttgagga gagccagacg      540
ttcggtctcg agatggacat cgtcgagggc atgcagtacg agcgcggcta catctccccg      600
tacatggcaa ccgacatgga gaagatggaa gccgtcctca agatcccta catcctcctt      660 accgaccaga aggtcaacaa catccaggac atggttccgc tgcttgaaga ggttatgaag      720
tccggtcgtc cgctgttcct cgtcgccgaa gacgtcgagg gcgaggcgct cgccaccatc      780
ctgctcaaca agctgcgcgg caccttcaac tgcgtcgcca tcaaggcccc cggcttcggc      840
gatcgtcgca agcgcatcct cgaggacatt gcggccgtta ccggcgcgca ggtcatcgac      900
aaggacttcg gcatgaccat ggccgatgcc accatcgata tgatgggcca cgcgaagacc      960
gtcaaggtca ccaaggacag cgcgctcatc gttgacggcg caggcgataa gaaggccatc     1020
gaggatcgca tccatcagat caaggccgag ctcgaccgcg tcgactccga cttcgatcgc     1080
gagaagctcc aggagcgctt ggccaagctc tccggcggcg ttgcggtgct caaggtgggc     1140
gctgctaccg aatcggagct caaggaaaag aagagccgca ttgaagatgc gctgcaggca     1200
acccgcgcag cggtcgaaga gggcatcgtt gccggcggcg gcgtggcgct tgtgaacgct     1260
atccccgcac tcgacaaggt tgaagtcgcc gacaaggacg aagaggtcgg cgtgagcatc     1320
```

```
gtccgcaagg cgcttgaggc tcccatgcgc gccattgctc aaaacgccgg tttcgaggga    1380
agcgtcgttg tcgagcacgt gaagggcatg aaggtcggcg aaggcctgaa ctgcgctacg    1440
ggcgagtatg gcaacatgat cgagatgggc gtgaacgatc cggtgaaggt tacccgtacg    1500
gcgctgcagt ctgccgcttc cgtgggtgcg ctcatcctca tcaccgaagc cacgatcaac    1560
gagatcccga aagagggccc cgacttgtct gcgctcgccg gtgctggcgg catgggcggg    1620
atgatgtag                                                             1629
```